United States Patent [19]
Floret

[11] Patent Number: 5,067,352
[45] Date of Patent: Nov. 26, 1991

[54] ULTRASONIC CONTROL HEAD FOR PARTS WHOSE SHAPE EVOLVES DURING PRODUCTION

[75] Inventor: Michel Floret, Gennevilliers, France
[73] Assignee: Aerospatiale Societe Nationale Industrielle, Gennevilliers, France
[21] Appl. No.: 469,846
[22] Filed: Jan. 24, 1990

[30] Foreign Application Priority Data

Feb. 2, 1989 [FR] France ............................. 89 01344
May 30, 1989 [FR] France ............................. 89 07110

[51] Int. Cl.⁵ .................... G01N 29/24; G01N 29/10
[52] U.S. Cl. .................................. 73/583; 73/625; 73/628; 73/640; 73/641
[58] Field of Search ............... 73/583, 625, 628, 640, 73/641, 644; 310/335, 336, 358

[56] References Cited

U.S. PATENT DOCUMENTS

| | | | |
|---|---|---|---|
| 3,350,925 | 11/1967 | Coy | 73/640 |
| 4,437,468 | 3/1984 | Sorenson et al. | 73/625 |
| 4,572,981 | 2/1986 | Zola | 310/358 |
| 4,715,228 | 12/1987 | Livsey et al. | 73/640 |
| 4,801,835 | 1/1989 | Nakaga et al. | 310/358 |

FOREIGN PATENT DOCUMENTS

958531 3/1950 France ............................. 73/644

Primary Examiner—Robert Raevis
Assistant Examiner—Rose M. Finley

[57] ABSTRACT

So as to control parts of any form, such as panels made of a composite material, a control head (10) is used comprising a small bar made of an elastic material, aligned ultrasonic transducers (18) being placed in said control head which functions by reflected light. The small bar bears contact blocks (22,24) which are brought into support on the surface of the part to be controlled, which has the effect of deforming the small bar and orientating each of the transducers perpendicular to the surface. As regards parts having a non-uniform shape, a uniform quality of the control is thus ensured, the same applying for a reduction of the control time. A precise control of the evolution of the structure of parts during production is also rendered possible. Advantageously, the transducers are mounted on the small bar so as to be disassembled, said mounting being effected by means of wedging members, such as screws and metal wire clips.

18 Claims, 5 Drawing Sheets

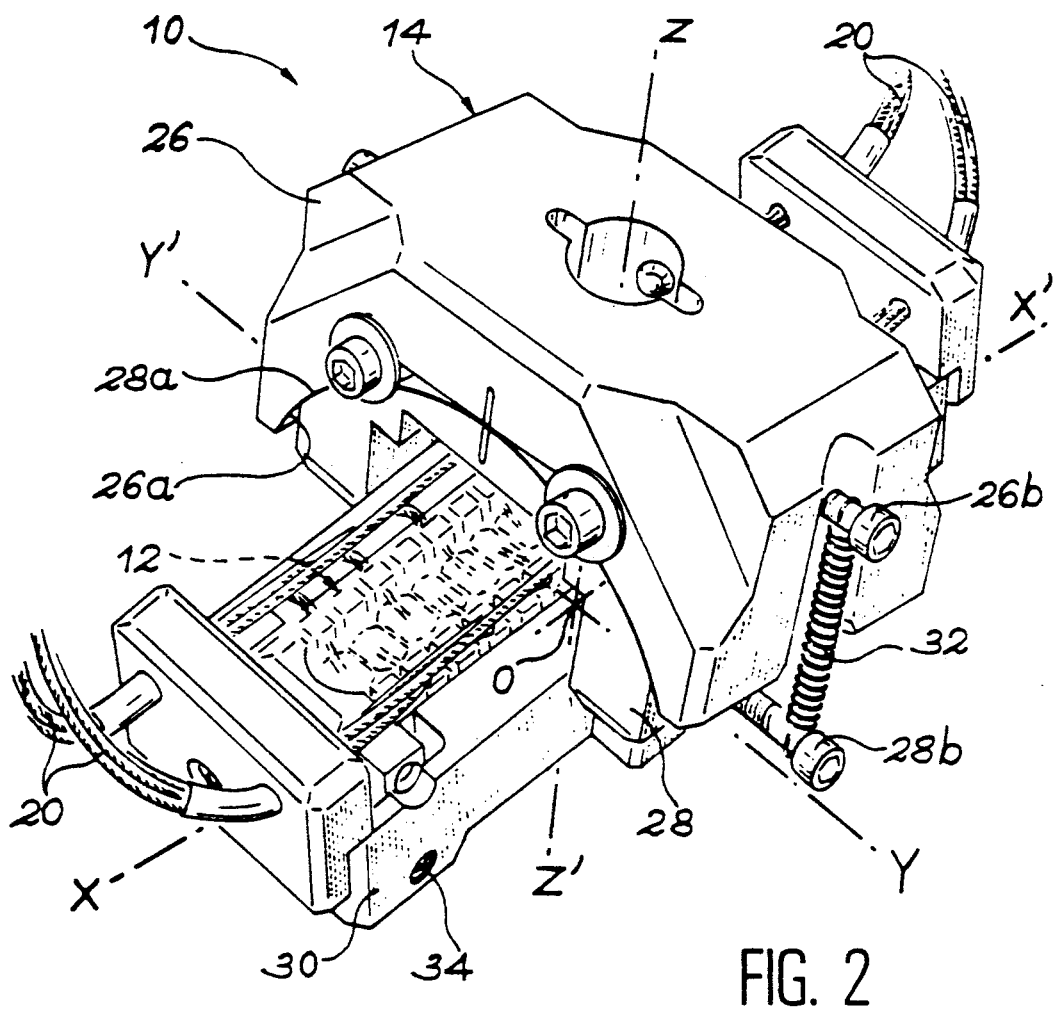
FIG. 2
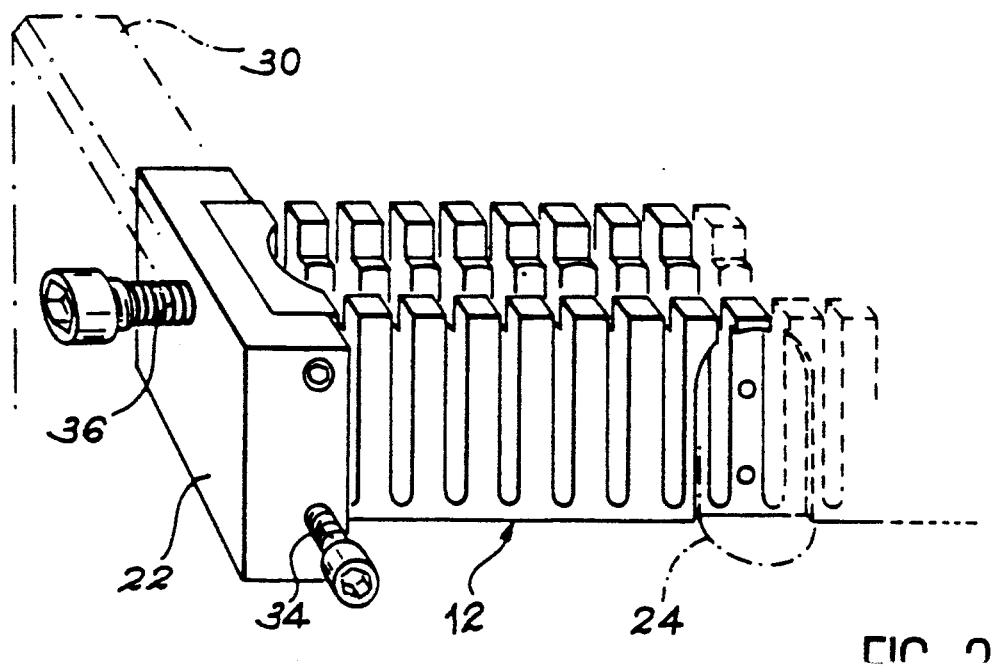

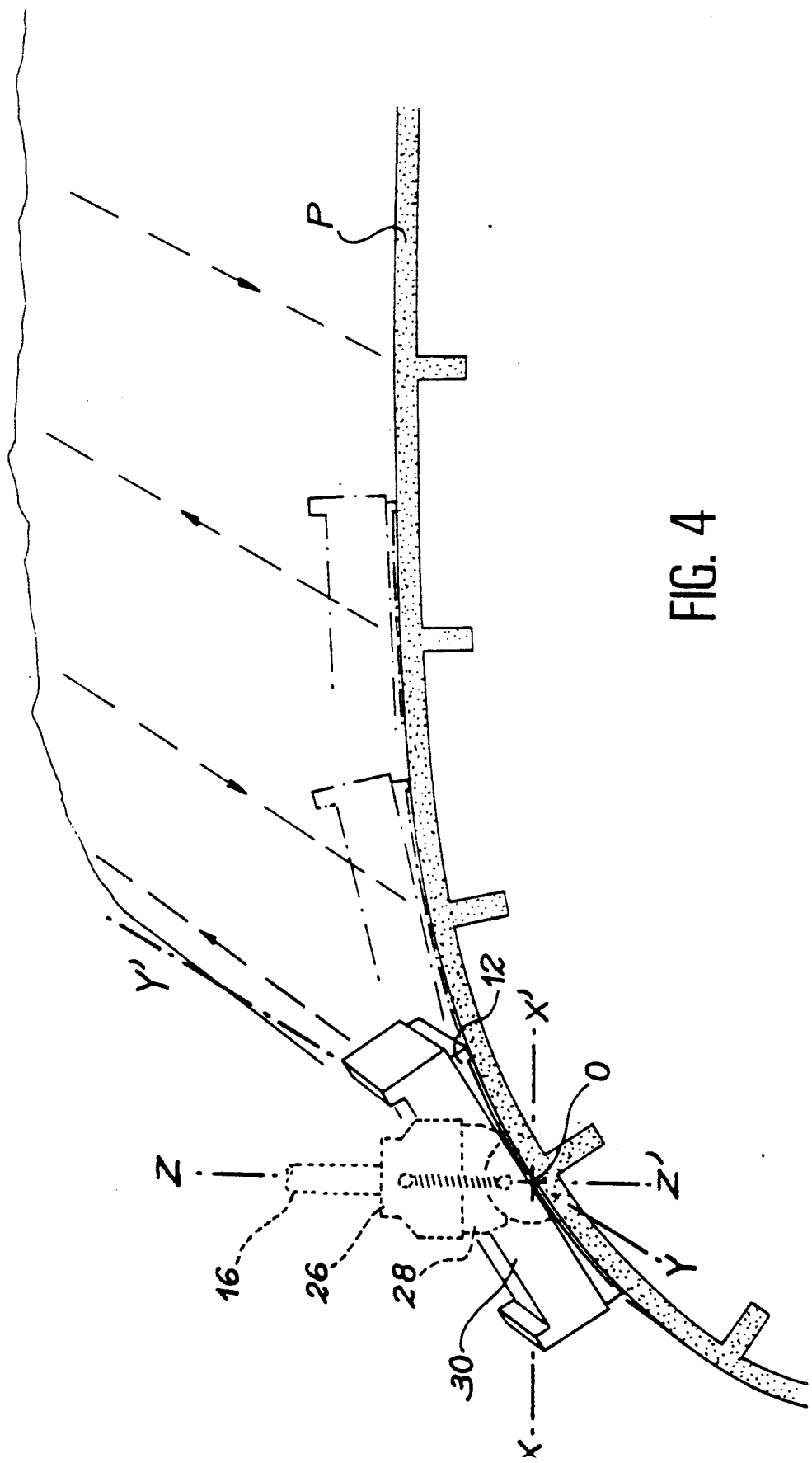

ULTRASONIC CONTROL HEAD FOR PARTS WHOSE SHAPE EVOLVES DURING PRODUCTION

FIELD OF THE INVENTION

The invention concerns a control head equipped with ultrasonic probes functioning by reflected light and making it possible to control parts of any shape, usually non-uniform, such as panels made of a composite material.

BACKGROUND OF THE INVENTION

The invention also concerns the application of such a control head for the embodiment of several successive controls on parts whose shape evolves during production at clearly defined points of these parts.

The use of parts made of a composite material has been considerably expanded over the last few years, especially as regards aeronautic, spatial, automobile, maritime and railway applications. This development is principally explained by virtue of the considerable lightening of structures it allows for and by the possibility offered by these materials so as to obtain complex shapes by means of moulding.

Parts made of a composite material are most often produced by the flat stretcher-levelling of several superimposed laps or layers, each formed of fibers impregnated with resin. Depending on the application involved, the fibers may be made of carbon, glass, Kevlar, etc. The resin constituting the matrix of the composite material is usually a duroplastic resin which polymerizes with the temperature. In particular, this polymerization may be obtained in a subsequent moulding stage during which the part is given its definitive shape.

Despite the afore-mentioned advantages, parts made of a composite material may have certain defects resulting from the particular structure of these materials. These defects originate from the lack of cohesion between the fibers resulting in the presence of air or gas pockets, possibly extensive ones. These are expressed on finished parts, either by a certain porosity of these parts when the pockets are small and distributed throughout the entire volume, or by a phenomenon, known as delamination, when the large air pockets are formed between the adjacent layers of the material.

The detection of these defects on finished parts is an operation required for the approval of these parts.

Furthermore, it is desirable to be able during production to monitor the evolution of defects and of the thickness of the part as its shape gradually varies. In fact, this monitoring makes it possible to optimize the conception of the starting structure of the flat stretch-levelled part.

So as to carry the non-destructive control of parts made of a composite material, original techniques have been developed, as conventional techniques for controlling metal parts, such as eddy current techniques, were not able to be applied to such parts. These techniques for controlling parts made of a composite material basically rely on the use of ultrasonic probes or transducers usually functioning at a frequency of between 0.5 and 15 MHz.

In particular and in the case of controlling parts with complex shapes, a reflected wave method is used in which the ultrasonic transducer is used both as a transmitter and a receiver. With the transducer being placed opposite the surface of the part, it receives in return the echoes sent back by this surface and by the surface opposite the part, as well as the echoes resulting from a possible delamination. Thus, it is possible to punctually control the thickness of the part and to detect the presence of delamination defects, as well as the position and extent of these defects. In addition, the measurement of the attenuation of the echo sent back by the surface opposite the part, corresponding to ultrasonic waves having twice traversed the thickness of said part, makes it possible to know the porosity of the structure.

As with all the ultrasonic control techniques, this reflected wave method has the drawback of being a punctual method so that the control of a large surface with the aid of a single transducer is a long and fastidious operation. If it is sought to reduce the control time and to group several transducers when a flat part or one with a uniform curve is being controlled, this objective has not been possible up until now when this involves controlling parts having a non-uniform shape, this frequently being the case with parts made of a composite material whose specific advantage is to make it possible to produce such parts.

In effect, the reflected wave control technique requires a relatively precise positioning of the transducers perpendicular to the surface of the part so that the echoes sent back by the surface of the part are properly received by the transducer. If this requirement may be satisfied relatively easily for a single transducer or for a group of transducers placed in relation to a flat surface or one with a uniform curve, this poses a problem which has never been resolved up until now when it is sought to combine several transducers so as to control parts having a non-uniform shape.

An even greater difficulty currently exists making it impossible to control, with the aid of a given control head comprising several transducers, a part whose shape evolves while being produced. In fact, along with the need for adaptation to the evolution of the shape of the part, there is a further difficulty of carrying out controls at points which remain unchanged whenever the shape changes.

SUMMARY OF THE INVENTION

The precise object of the invention is to provide a control head with an original conception and grouping several ultrasonic transducers so that each transducer remains approximately perpendicular to the surface of the part to be controlled and controls points whose spacing remains invariable, irrespective of the shape of this surface and the evolution of this shape in terms of time and space.

According to the invention, this first objective is attained by means of a head for ultrasonic controlling parts of any shape, wherein it includes a ductile small bar supporting a set of ultrasonic transducers with coplanar axes and functioning by reflected light, as well as contact blocks distributed along the small bar and being suitably adapted so as to be simultaneously brought into support on one surface of the part to be controlled, so that the axes of all the transducers are approximately perpendicular to this surface and cut the surface at separate points by approximately constant distances independent of the shape of the part.

According to one preferred embodiment of the invention, the ductile small bar is made of an elastic material and in the rest position has a given curve along said direction. More precisely, the ductile small bar has roughly the shape of a comb comprising a linking branch with a variable curve suitable for being turned towards the part and teeth remaining approximately perpendicular to the linking branch and in which each transducer is housed.

Preferably and so as to avoid having to change the entire small bar if one of the transducers no longer functions correctly and when the number and/or the characteristics of the transducers need to be modified, each transducer is mounted onto the small bar so as to be able to be moved by dismountable fixing means.

Advantageously, these dismountable fixing means include wedging members, such as screws, traversing the small bar and whose extremities penetrate into holes formed in the lateral faces of a box encasing each of the transducers.

In addition to these wedging members, the fixing means preferably include for each transducer a linking member, such as a metal wire, connecting the extremities of the two parts of each tooth of the small bar and between which the transducer is housed.

So that each transducer may be perfectly marked geometrically with respect to a reference frame linked to a carrier supporting the control head, the control head further includes a rotating unit supporting the ductile small bar and defining two hinge pins whose point of intersection is situated on one axis of a central transducer close to the surface of the part where the blocks are in support.

Depending on the nature of the part to be controlled, the transducers borne by the small bar may be identical or not. In these two cases, they are advantageously connected to multiplexing means making it possible to successively control each zone of the part and situated opposite each transducers. By using transducers mounted in the small bar so as to transmit ultrasonic beams tangent to each other, it is thus possible to control by scanning a large part with a variable shape in an extremely short space of time compared with the time required to control such parts by means of a single transducer.

The invention also concerns using this control head to carry out several successive controls on parts whose shape evolves while being produced from an approximately initial flat state. According to this application, a method is proposed consisting of:
marking out on the part when in its initial state points to be controlled and distributed according to a predetermined meshing; and
controlling the part in its initial state and then at least once again during production by means of a single ultrasonic control head according to the invention by aligning the axes of the transducers of the control head with the points to be controlled.

BRIEF DESCRIPTION OF THE DRAWINGS

One preferred embodiment of the invention shall now be described, by way of example in no way restrictive, with reference to the accompanying drawings in which:

FIG. 2 is a perspective view of the control head of FIG. 1 taken from the top;

FIG. 3 is a perspective view representing the ductile small bar in the shape of a comb in which the ultrasonic transducers of the control head of FIGS. 1 and 2 are normally housed;

FIG. 4 is a side view diagrammatically illustrating the control head of the invention so as to control a panel made of a composite material having a non-uniform shape;

DETAILED DESCRIPTION OF THE PREFERRED EMBODIMENTS

Figure 1:
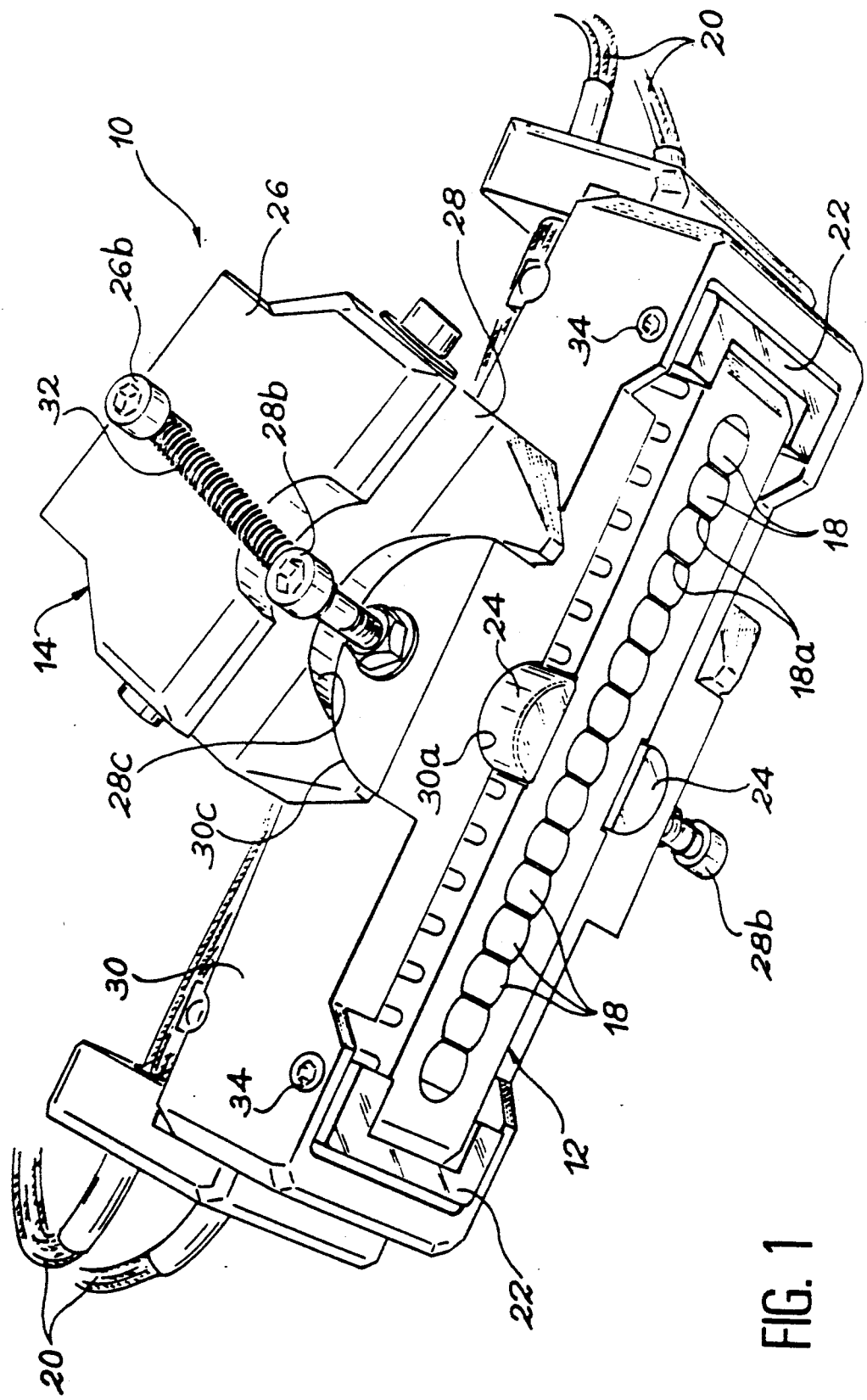
FIG. 1 is a perspective view representing an ultrasonic control head according to the invention, this view being taken underneath, that is on the side of the head turned towards the part to be controlled.

On FIGS. 1 to 5, the control head of the invention is generally denoted by the reference 10. This control head 10 essentially includes a ductile small bar 12 and a rotating unit 14 supporting the small bar 12 and enabling it to be mounted on a carrier whose extremity bears the reference 16 on FIG. 4.

The ductile small bar 12, whose structure shall subsequently be described in more detail, supports a set of ultrasonic transducers 18 aligned along a direction coinciding with the length of the small bar. Each of these transducers 18 makes it possible to carry out independently of the others a reflected light measurement by means of a conventional electronic circuit (not shown), which does not form part of the invention, via a multiplexing system (not shown) enabling each transducer to control in turn the zone of the part situated opposite this transducer.

The structure of the transducers 18 does not form part of the invention. However, each transducer includes an ultrasonic emitting piezoelectric pellet, a damping element being placed behind the pellet and a relay being placed in front of said pellet. An ultrasonic transducer thus constructed generally has a cylindrical configuration and its axis needs to be oriented approximately perpendicular to the surface of the part to be controlled so that the echo of the ultrasonics emitted by the piezoelectric pellet and reflected by the part return onto this transducer.

So that the alignment of the transducers 18 mounted in the small bar 12 allows for scanning of all the zone situated opposite this small bar, these transducers are preferably mounted in the bar so as to emit ultrasonic beams tangent to each other. To this effect and as shown on FIG. 1, lateral faces 18a, being both flat and parallel to each other, are machined on each of the transducers, the transducer being mounted in the small bar 12 so that the extremities of the transducers turned towards the part to be controlled are virtually in contact with each other via these faces 18a.

Depending on the type of control to be carried out, the transducers 18 may have identical characteristics or, on the other hand, may differ from one transducer to another.

As shown in more detail on FIG. 3, the small bar 12 supporting the transducers 18 roughly has the shape of a comb made of an elastic material. The lower face of the small bar turned towards the part to be controlled, on which the extremity faces of each of the transducers are made flush, have in the rest position a determined curve or camber, for example one with an infinite radius (that is, flat). This lower face is formed on the linking branch of the comb formed by the small bar when the teeth of this comb, which project towards the rear from the linking branch, each support one of the transducers 18. This configuration allows for an elastic deformation of the small bar outside its aforesaid rest position and having the effect of giving the lower face of the small bar a variable curve which may be adapted to the curve of the part to be controlled, as shall be seen subsequently. This deformation may be made within a range of determined curves, for example between one curve at rest with an infinite radius and a maximum deformation curve with a radius of close to 300 mm in the concave direction.

In practice, the material constituting the comb 12 is selected so as to give the small bar the elasticity desired while ensuring effective holding of the transducers by glueing and satisfactory sealing of the electric connections between the transducers and the electric connecting wires 20 (FIG. 2) whereby the transducers are connected to the associated electronic circuit. Advantageously, a plastic material shall be used for this purpose, said plastic being a silicon-based plastic.

As shown in particular on FIG. 1, the ductile small bar 12 is equipped with contact blocks 22 and 24 distributed over the length of the bar 12. These blocks 22, 24 are suitably adapted for taking support on the surface of the part to be controlled so as to give the small bar a curve comparable to the curve of this surface, whatever this curve may be inside the range of acceptable curves as regards the small bar.

In the embodiment example shown on the figures, these contact blocks include two U-shaped extremity blocks which are mounted by being fitted onto each of the extremities of the small bar 12. In addition, two lateral blocks 24 with a circular-shaped sector are mounted at the center of each of the sides of the small bar 12 with their cylindrical faces turned outwardly and whose axes are orientated perpendicular to the lower face of the small bar. The blocks 22 and 24 are mounted so as to be interchangeable on the small bar 12 and project beyond the lower face of the bar 12 over a given distance. This distance, limited to several millimeters, is adjustable.

Given the fact that the contact blocks 22 and 24 are distributed over the length of the small bar 12, when these blocks are all in support on the surface of the part to be controlled, this means that the curve of the lower face of the small bar is approximately the same as the curve of the zone of the part situated opposite the control head. It is then virtually ensured that the axis of each of the transducers 18 is approximately perpendicular to the surface of the part situated opposite this transducer and that the distance between the extremity of each transducer and the surface opposite is virtually the same for each transducer. Thus, the conditions for the functioning of each transducer 18 are identical from one extremity to the other of the small bar, even if the curve of the part varies. As a result, the control head of the invention makes it possible to carry out measurements in virtually uniform conditions for each transducer and over the entire surface of the part.

Furthermore, the extremity of the transducers is sufficiently close to the surface of the part so that the distance separating the points of intersection of the axes of the transducers with the surface of the part may be regarded as approximately constant or invariable, irrespective of the shape of the part. This property is particularly useful in the application of the invention and shall be described subsequently with reference to FIGS. 5A and 5B.

As clearly shown on FIGS. 1, 2 and 4, the rotating unit 14, whereby the small bar 12 is mounted at the extremity of the carrier 16, includes a support 26 provided so as to be mounted at the extremity of the carrier 16, an intermediate part 28 and a frame 30.

The support 26 cooperates with the intermediate part 28 via two surfaces of revolution 26a and 28a (FIG. 2), respectively concave and convex, and giving the intermediate part 28 a degree of freedom of rotation with respect to the support 26 around a hinge pin XX' perpendicular to the axis ZZ', generally vertical, of the extremity of the carrier 16. This rotational axis XX' is contained within a plane passing through the axes of each of the transducers 18 and the axis ZZ'.

On each of the sides of the support 26 and the intermediate part 28, anchorage blocks 26b, 28b project perpendicular to the axes XX' and ZZ' and on which hooked are two return springs 32 which have the effect of normally keeping the intermediate part 28 in a central rest position, as shown on FIG. 2.

The intermediate part 28 overlaps the frame 30 and cooperates with the latter on both sides of the frame by additional surfaces of revolution 28c and 30c, respectively concave and convex. The surfaces of revolution 28c and 30c define a second rotational axis YY' orthogonal to the axis XX' and appearing on FIG. 2.

According to a particularly advantageous characteristic of the described embodiment, the axes XX', YY' and ZZ' are cut at a given point 0 which is situated close to the surface of the part where the blocks 22 and 24 are in support (FIG. 4). More precisely, this point 0 is situated in the middle of a segment formed by the intersections of the axis of the central transducer with the surface of the part where the blocks 22 and 24 are in support respectively when the small bar has its rest curve and when the small bar has its maximum deformation curve.

As a result and solely by way of example, if the curve at rest of the small bar corresponds to an infinite radius, if the maximum deformation curve corresponds to a radius of about 300 mm and if a control head is used comprising fifteen sensors whose center distance of axes is about 6.8 mm, the maximum distance between the point of intersection of the axes XX' and YY' is at the most equal to about 2 mm with respect to the surface of the part.

This characteristic makes it possible to accurately know, independently of the particular curve of the controlled zone, the coordinates of the various points of the surface currently being controlled without it being necessary to add to the control head a complex coordinate calculation unit.

The small bar 12 is itself mounted in the frame 30 by two spindles 34 perpendicular to the axes XX' and ZZ' and traversing the extremities of the small bar immediately close to the lower face of the small bar. In its central section, the frame 30 comprises internal grooves 30a (FIG. 1) with an arc of a circle section, said grooves being orientated along a direction perpendicular to the spindles 34 and to the lower face of the small bar, the lateral blocks 24 sliding into said grooves when the small bar gets out of shape.

Preferably and as shown on FIG. 3, so as to guarantee the return of the small bar 12 into its rest position, in spite of the hysteresis possibly existing in the material constituting said bar, return springs 36 are inserted between the frame 30 of each of the extremities of the small bar 12 within a plane offset towards the rear with respect to the lower surface of the latter.

As shown diagrammatically on FIG. 4, the control head 10 of the invention makes it possible to control by successive scannings a panel P made of a composite material, such as an aircraft wing unit element whose curve varies progressively, whilst allowing for a considerable gain of time with respect to conventional control techniques.

In order to embody control by ultrasonics, a coupling fluid, such a water, needs to be present between each transducer and the surface of the part to be controlled. To this effect, the part is preferably placed in a swimming pool. As a variant, a system for injecting the coupling fluid may, however, be added to the control head.

So as to carry out the actual control, the control head may advantageously move along the direction YY' after having prevented any movement in the direction XX'. Then each block borne by the small bar 12 is brought into contact with the surface of the panel to be controlled at one extremity of the latter by lowering the control head along the direction ZZ' with the aid of the carrier 16. When this contact is established, this means, as seen previously, that each transducer 18 is positioned satisfactorily with respect to the surface of the panel.

The actual control, which may merely be a control of thickness, a quality control or both these controls combined, can then be effected over the entire width of the strip scanned by the control head by moving the latter progressively along the direction YY' as far as the other extremity of the panel. During this movement, a slight prestressing applied by the carrier to the head 10 guarantees the continuous application of the blocks onto the surface of the panel and accordingly the precision of the control.

When a first strip of the panel has thus been controlled, the control head is moved along the direction XX' by a distance equal to the width of the strip scanned by the head. A second strip of the panel may then be controlled in the same way as previously. The operation is repeated until the panel to be controlled has been completely scanned.

In practice, the operation just described and explained briefly above can be embodied extremely simply by mounting the carrier 16 on a portico suitable for being moved on rails over the entire length of the panel by means of a carriage able to occupy different predetermined positions on the portico and by equipping the carrier 16 with a device, such as a thrustor, applying to the control head 10 a moderate force towards the bottom.

Figure 5A:
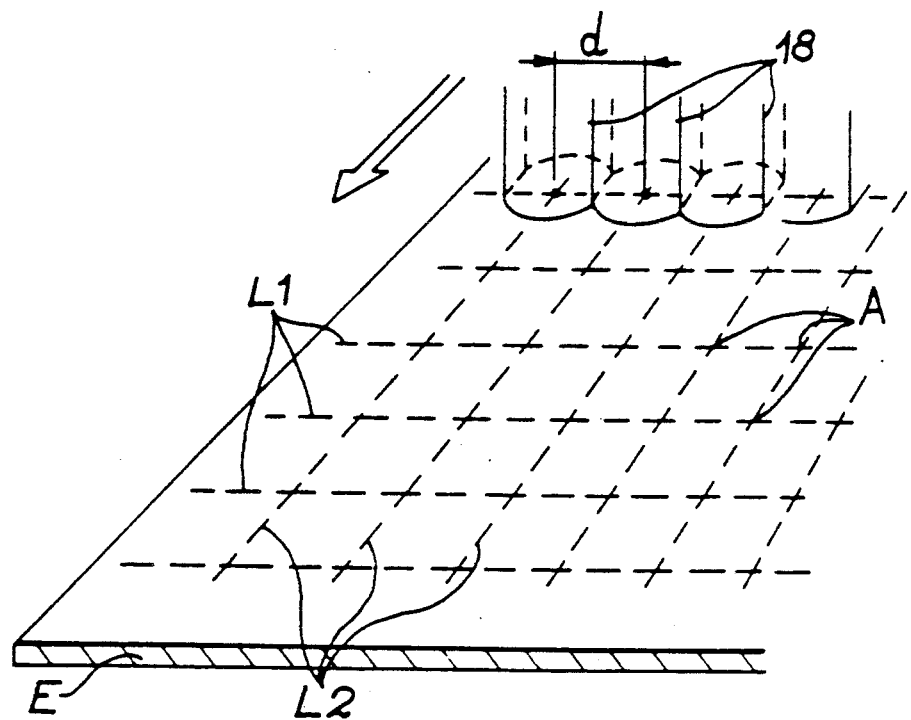
FIGS. 5A and 5B are perspective views diagrammatically illustrating the carrying out of successive controls of a panel made of a composite material respectively in its initial state and then at another stage of its production when it has a different shape, these controls being effected with the aid of the control head of FIG. 1.
Figure 5B:
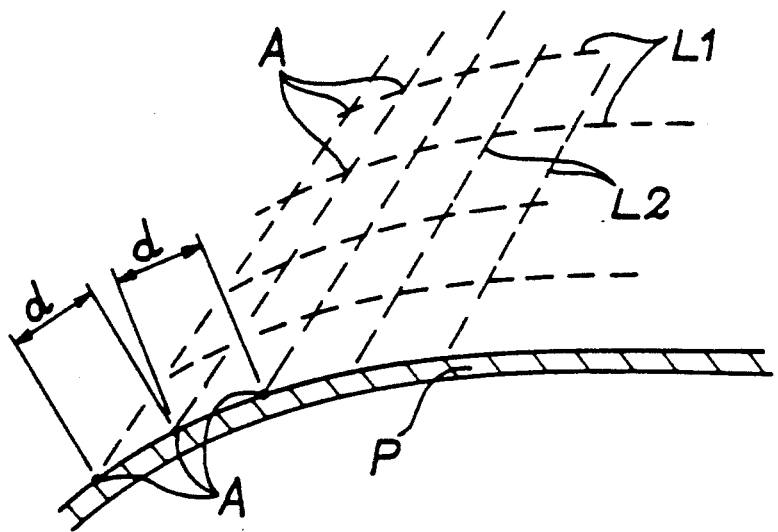

FIGS. 5A and 5B clearly diagrammatically show one particularly advatageous application of the control head of the invention for the embodiment of several successive controls on a part made of a composite material when being produced.

During the production of certain parts made of composite materials, an approximately flat blank is embodied by stretcher-levelling before giving the part its final shape, for example by moulding. By using the control head described previously, at various moments when the part is being produced, it is possible to observe both the evolution of the thickness of the part and the growth of the defects it contains at precise points and which remain the same, irrespective of the shape of the part.

To this effect and as shown on FIG. 5A, when the roughly flat blank of the part E has been embodied, a meshing is marked out on the surface of this blank, said meshing formed by two series of parallel lines L1 and L2 orthogonal to each other cut at the points A. These points A determine those points where a control needs to be carried out. The spacing between the lines L2 adjacent to one of the sets of lines is selected so as to be equal to the distance d separating the axes of the transducers 18 adjacent to the control head when these axes are parallel.

This distance d is measured along a straight line when the small bar is applied to a flat surface and along a curve corresponding to the shape of the surface (when the small bar is applied to a shaped surface). However, this "curved distance" is as regards a first approximation virtually equal to a linear distance.

When this marking out is completed, a first control is effected by means of the previously described control head with reference to FIGS. 1 to 3. To this effect, the blocks 22 and 24 are brought into contact with the part and the head is positioned so that the axes of each of the transducers 18 cut one of the lines L2. By moving the head parallel to these lines L2, the axes of the transducers are successively brought above each of the alignments of the points A to be controlled placed on the lines L2 by each time carrying out all the measurements permitted by the transducers.

The production of the part P is then continued from the blank E by conventional means so as to give it at during one or more operations the desired shape. As shown on FIG. 5B, at the end of each operation, the control head of the invention allows the previous measurements to be repeated at virtually the same places, that is at the location of the points A. In fact and as described earlier, the disposition of the transducers 18 on the control head makes it possible to roughly retain the distances d which separate the intersections of the axes of the adjacent transducers with the surface of the part independent of the shape given to this surface.

The possibility thus offered by the invention, namely to carry out at clearly determined points of the part several successive controls at various stages for the production of a part made of a composite material, is a particularly advantageous one. The evolutions of defects and thickness occuring during production can in fact disclose certain defects concerning the conception of the starting structure constituted by the blank E. The observation of these evolutions thus makes it possible to optimize the design of this starting structure and, as a result, to improve the part obtained.

Figure 6:
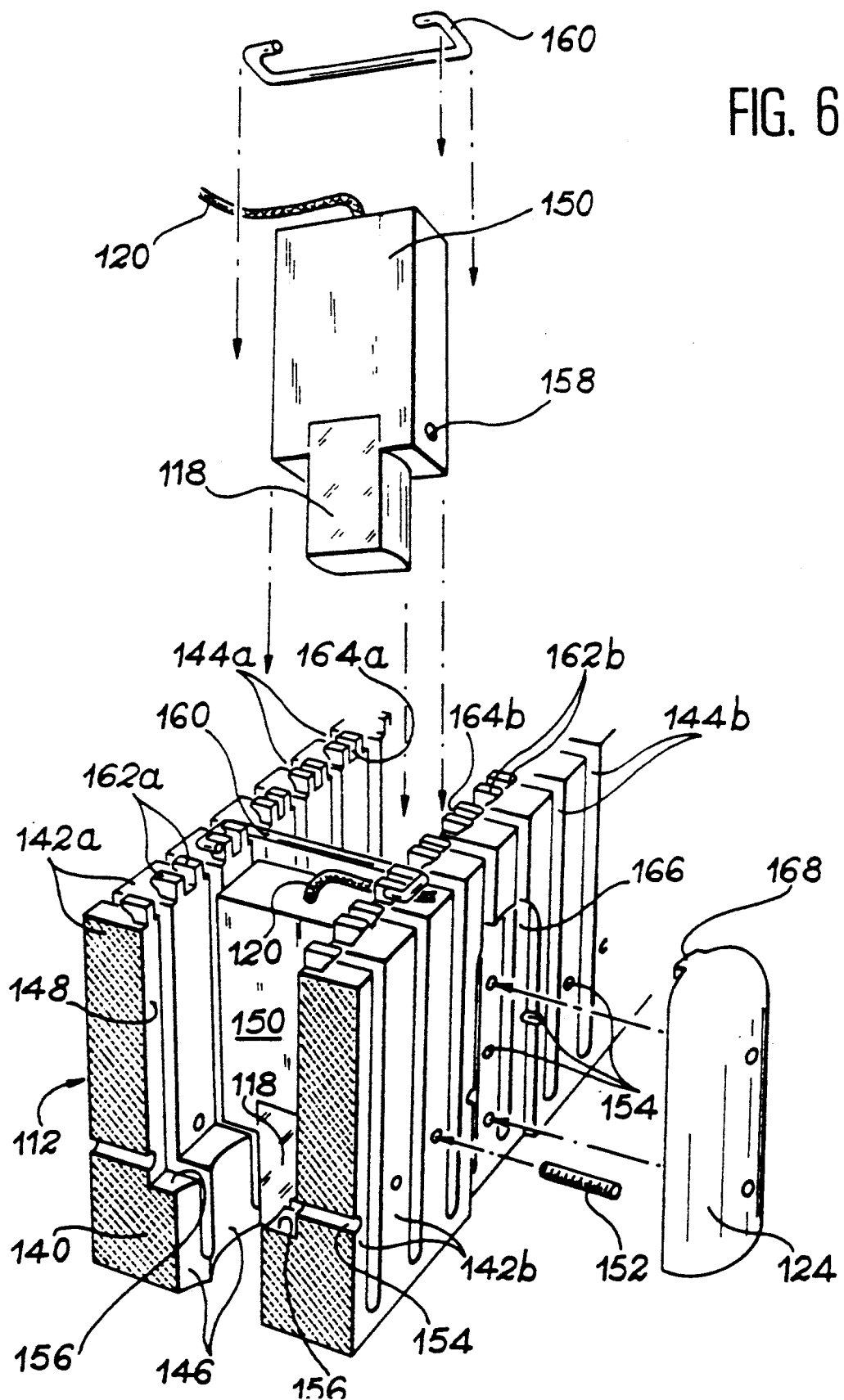
FIG. 6 is an exploded perspective view representing the central section of a ductile small bar in which the transducers are mounted in such a way that they can be moved.

FIG. 6 shows an embodiment variant concerning the small bar and in which each transducer is mounted so as to be able to be moved.

Accordingly, the reference 112 on FIG. 6 generally denotes the central section of a ductile small bar made of a flexible material. This small bar 112 is provided so as to be mounted onto a rotating unit (not shown) similar to the one previously described with reference to FIGS. 1 and 2.

The ductile small bar 112 roughly has the shape of a comb whose lower face, turned towards the part to be controlled, is formed on a linking branch 140 of the small bar. This linking branch 140 bears teeth formed of two arms 142a and 142b orientated perpendicular to the linking branch and separated respectively by apertures 144a and 144b.

The linking branch 140 has a central opening which is approximately rectangular and whose two sides, orientated according to the length of the small bar, being formed by the juxtaposition of surfaces 146 having as a section the shape of arcs of a circle parallel to the lower face of the linking branch. Each of these surfaces 146 corresponds to one of the teeth of the small bar.

The two arms 142a and 142b of the teeth of the comb formed by the small bar 112 have flat and parallel internal faces 148 whose spacing is larger than the one separating the arc of a circle-shaped surfaces 146. A shoulder 156 parallel to the lower face of the small bar connects the surfaces 146 to the faces 148.

As in the case of the embodiment previously described, several transducers 118 are mounted side by side in the small bar 112. More precisely, a transducer 118 is mounted between the two arms 142a and 142b of each of the teeth, its extremity being received in the central opening of the linking branch 140, so that its extremity face is level with the lower face of this branch.

Each transducer 118 has the shape of a cylinder with an axis perpendicular to the lower face of the linking branch 140 and on which opposing parallel faces are machined via which the transducers are juxtaposed. Furthermore, each transducer 118 is mounted in a sealed casing box 150 made, for example, of resin, except for its extremity turned towards the part to be controlled, said extremity being received between the arc of a circle-shaped surfaces 146 formed in the linking branch 140. The sealed casing box 150 has a parallelpiped shape and is received between the flat faces 148 opposite the arms 142a and 142b of the teeth.

So as to allow for the subsequent replacement of the unit formed by each transducer 118 and its casing box 150, each of these units is mounted in the small bar 112 so as to be able to moved by means of dismountable fixing means.

In the embodiment shown on FIG. 6, these dismounting fixing means include screws 152 which are screwed into tapped holes 154 traversing each of the parts 142 immediatedly above the shoulders 156 separating the faces 148 of the surfaces 146. The extremities of these screws 152 penetrate into the holes 158 formed on each of the lateral faces of the casing boxes 150.

Advantageously, the dismountable fixing means further include linking members constituted by metal wire clips 160 which connect the two arms 142a and 142b of each tooth at their extremities opposite the linking branch 140. Each clip roughly has the shape of a C whose extremities are hooked onto sections 162a and 162b with the shape of hooks constituting the extremity of each of the arms 142a and 142b.

Each of the hook-shaped sections 162a and 162b has a notch 164a, 164b able to be moved into by an electric conductor 120 coming out via the rear face of each of the casing boxes 150.

When a transducer 118 is put in place, it is firstly positioned and rendered immobile close to the lower face of the small bar by means of the screws 152. The corresponding clip 160 is then placed, which has the effect of cladding the arms 142a and 142b against the lateral faces of the casing box 150 of the transducer and of retaining the position of the electric conductor 120.

By means of the disposition described above, it is possible to replace a defective transducer without having to replace the entire small bar.

In addition, it is also possible to carry out different controls with the aid of a given small bar by replacing one or several of the transducers by transducers having different characteristics or even by spurious transducers not having any control function.

On the other hand, this disposition makes it possible to recover the transducers when the small bar is damaged and needs to be replaced.

Thus, a control head is embodied whose elements are interchangeable and expendable.

As shown on FIG. 6, each of the contact blocks 124 mounted on both sides of the small bar 112 at the center of the latter is fixed into a stiffener 166 overlapping three adjacent teeth of the comb, for example by means of two screws (not shown) screwed into the central tooth. So as to ensure that this fixing does not prevent any relative deformation between these three teeth, the face of each of the blocks 124 turned towards the small bar comprises an overhanging section 168 which is in contact with the bottom of the stiffener 166 solely in the section of the latter formed on the central tooth.

Of course, the invention is not merely limited to the embodiments described above by way of examples, but also covers all its variants.

Thus, one can clearly and easily see that a control head according to the invention may be used to indifferently control parts with a concave or convex shape or even parts whose shape evolves between a flat shape, a slightly convex shape and a slightly concave shape. In certain particular cases and especially when the control head of the invention is used to control the inside of an angle, the small bar bearing the transducers is merely required to be only partly ductile as regards the zone(s) where the curve of the part varies. Moreover, the transducers equipping a given small bar may have different characteristics and the distances separating the axes of these transducers may also be different. Finally, when the transducers are interchangeable, the screws ensuring their locking may be replaced by equivalent wedging means.

What is claimed is:

1. Head for control by ultrasonics of parts of any shape and comprising a ductile small bar which supports a set of ultrasonic transducers with coplanar axes and functioning by a reflected wave, said ductile small bar being made of an elastic material and at rest presents a curve along a longitudinal direction of said bar, and contact blocks distributed along the small bar and being suitably-adapted to be brought simultaneously into support on a surface of a part to be controlled so that the axes of all the transducers are approximately perpendicular to this surface and cut said surface at points separated by approximately constant distances independent of the shape of said part, wherein the ductile small bar roughly forms a comb comprising a linking branch with a variable curve and suitable for being turned towards said part, and teeth remaining approximately perpendicular to the linking branch and housing each of the transducers.

2. Head for control by ultrasonics of parts of any shape and comprising a ductile small bar which supports a set of ultrasonic transducers with coplanar axes and functioning by a reflected wave, said ductile small bar is made of an elastic material and at rest presents a curve along a longitudinal direction of said bar and contact blocks distributed along the small bar and being suitably-adapted to be brought simultaneously into support on a surface of a part to be controlled so that the axes of all the transducers are approximately perpendicular to this surface and cut said surface at points separated by approximately constant distances independent of the shape of said part, means for returning the ductile small bar to its rest position.

3. Head for control by ultrasonics of parts of any shape and comprising a ductile small bar which supports a set of ultrasonic transducers with coplanar axes and functioning by a reflected wave, and contact blocks distributed along the small bar and being suitably-adapted to be brought simultaneously into support on a surface of a part to be controlled so that the axes of all the transducers are approximately perpendicular to this surface and cut said surface at points separated by approximately constant distances independent of the shape of said part, wherein said bar supports an odd number of transducers, said control head further including a rotating unit supporting the ductile small bar and defining two hinge pins whose point of intersection is situated on one axis of a central transducer of said transducers close to said surface of said parts.

4. Control head according to claim 3, wherein the small bar is able to be warped between a curve at rest and a maximum deformation curve, the point of intersection of the hinge pins being situated roughly in the middle of a segment formed by the intersections of the axis of said central transducer with the surface of a part where these blocks are in support respectively for said rest curve and said maximum deformation curve of the small bar.

5. Control head according to claim 3, wherein the rotating unit includes a support suitable for being mounted on a carrier, an intermediate part and a frame on which the small bar is mounted, the intermediate part being in contact with the support and with the frame via additional surfaces of revolution centered on said hinge pins.

6. Control head according to claim 5, wherein the small bar is mounted on the rotating unit via its two extremities by means of two spindles parallel to one of the hinge pins.

7. Control head according to claim 6, wherein the contact blocks include two U-shaped extremity blocks mounted on each extremity of the small bar and two lateral blocks with a circular sector shaped section mounted at the center on each side of the small bar so as to be able to slide along an axis parallel to the axis of said central transducer into an arc of circle-shaped grooves formed in said frame.

8. Head for control of ultrasonics of parts of any shape and comprising a ductile small bar which supports a set of ultrasonic transducers with coplanar axes and functioning by a reflected wave, and contact blocks distributed along the small bar and being suitably-adapted to be brought simultaneously into support on a surface of a part to be controlled so that the axes of all the transducers are approximately perpendicular to this surface and cut said surface at points separated by approximately constant distances independent of the shape of said part, wherein the transducers are mounted into the small bar so as to emit ultrasonic beams tangent to each other, and the transducers have adjacent flat lateral faces.

9. Head for control by ultrasonics of parts of any shape and comprising a ductile small bar which supports a set of ultrasonic transducers with coplanar axes and functioning by a reflected wave, and contract blocks distributed along the small bar and being suitably-adapted to be brought simultaneously into support on a surface of a part to be controlled so that the axes of all the transducers are approximately perpendicular to this surface and cut said surface at points separated by approximately constant distances independent of the shape of said part wherein the contact blocks are interchangeable.

10. Head for control by ultrasonics of parts of any shape and comprising a ductile small bar which supports a set of ultrasonic transducers with coplanar axes and functioning by a reflected wave, and contract blocks distributed along the small bar and being suitably-adapted to be brought simultaneously into support on a surface of a part to be controlled so that the axes of all the transducers are approximately perpendicular to this surface and cut said surface at points separated by approximately constant distances independent of the shape of said part, wherein each of said transducers is mounted on the small bar by dismountable fixing means and the dismountable fixing means include wedging members traversing the small bar and whose extremities penetrate into holes formed in the lateral faces of a casing box of each of the transducers.

11. Control head according to claim 10, wherein the casing box is a sealed parallelpiped box which encases the major part of each transducer, except for the extremity of said transducer opposite the surface of said part, holes being formed in the casing box close to this extremity of each transducer.

12. Control head according to claim 10, wherein the wedging members are screws.

13. Control head according to claim 10, wherein the ductile small bar is made of an elastic material and forms a comb comprising a linking branch with a variable curve turned towards said part, and teeth perpendicular to the linking branch, each tooth including two arms between which one of the transducers is housed, the dismountable fixing means further including a linking member connecting the extremities of the two arms of each tooth opposite the linking branch.

14. Control head according to claim 13, wherein each linking member is constituted by a metal wire clip encompassing said extremities of the two arms of each tooth, these extremities form hooks.

15. Control head according to claim 14, wherein each hook-shaped extremity has a notch in which an electric conductor coming out of the corresponding transducer is normally kept in place by said metal wire clip.

16. Method for the ultrasonic control of parts whose shape evolves during their production from a roughly flat initial state and consisting of:
when in its initial state, marking out on said part points to be controlled and distributed according to a predetermined meshing; and
controlling said part in its initial state at least once when being produced by means of a single ultrasonic control head comprising a ductile small bar which supports a set of ultrasonic transducers with coplanar axes and functioning by reflected light, and contact blocks distributed along the small bar and being suitably-adapted to be brought simultaneously into support on a surface of a part to be controlled so that the axes of all the transducers are approximately perpendicular to this surface and cut said surface at points separated by approximately constant distances independent of the shape of said part, said distances being substantially equal to distances between said points previously marked out on said part, whereby controlling is performed by applying the control head on said surface in such a way that the axes of the transducers are aligned with said points.

17. Control head according to claim 1, wherein the transducers are mounted into the small bar so as to emit ultrasonic beams tangent to each other.

18. Control head according to claim 1, wherein each of said transducers is mounted on the small bar by dismountable fixing means.

* * * * *